United States Patent
May et al.

(10) Patent No.: US 6,495,514 B1
(45) Date of Patent: Dec. 17, 2002

(54) METHOD FOR REDUCING INFLAMMATION AND INDUCING AN ANALGESIC EFFECT AND COMPOUNDS THEREOF

(75) Inventors: Sheldon W. May; Stanley H. Pollock, both of Atlanta, GA (US)

(73) Assignee: Mercer University, Macon, GA (US)

( * ) Notice: Subject to any disclaimer, the term of this patent is extended or adjusted under 35 U.S.C. 154(b) by 0 days.

(21) Appl. No.: 09/010,162

(22) Filed: Jan. 21, 1998

(51) Int. Cl.[7] .......................... A61K 38/00; A61K 31/19
(52) U.S. Cl. .......................... 514/2; 514/557; 514/578; 514/825; 514/886; 514/19
(58) Field of Search .............................. 514/2, 557, 19, 514/578, 825, 886

(56) References Cited

PUBLICATIONS

Ogonowski et al., FASEB J. vol. 9, No. 4 p. A956, Apr. 1995.*
Bundgaard, Design of Prodrugs (Elsevier Publishing) Ch. 1 pp. 1–10, 1985.*
Matucci–Cerinice et al.: "The Contribution of the peripheral nervous system and the neuropeptide network to the development of synovial inflammation." Clinical and Experimental Rheumatology 10:pp. 211–215, 1992.
Panagakos et al."Modulation of Carrageenan–Induced Hind Paw Edema by Substance P." Inflammation. vol. 18. No. 3, pp 285–292, 1994.
Bradbury, A.F., Finnie, M.D.A. and Smyth, D.G.: Mechanism of C–terminal amide formation by pituitary enzymes. Nature 298: 686–688, 1982.
Colpaert, F.C., Donner, J. and Lembeck, F.: Effects of capsaicin on inflammation and on the substance P content of nervous tissue in rate with adjuvant arthritis. Life Sci. 32: 1827–1834, 1983.
Cronstein, B.N. and Weissmann, G.: Targets for antiinflammatory drugs. Annu. Rev. Pharmacol. Toxicol. 35: 449–462, 1995.
DiRosa, M., Giroud, J.P. and Willoughby, D.A.: Studies of the mediators of the acute inflammatory response induced in rats in different sites by carrageenan and turpentine. J. Pathol 104: 15–29, 1971.
Doherty, N.S., Beaver, T.H., Chan, K.Y., Coutant, J.E. and Westrich, G.L.: The role of prostaglandins in the nociceptive response induced by intraperitoneal injection of zymosan in mice. Br. J. Pharmacol. 91: 39–47, 1987.
Dray, A. and Perkins, M.: Bradykinin and inflammatory pain. Trends Neurosci. 61: 99–104, 1993.
Gamse, R.: Capsaicin and nociception in the rat and mouse. Possible role of substance. P. Naunyn–Schmiedeberg Arch. Pharmacol. 320: 205–216, 1982, p206.
Garry, M.G. and Hargreaves, K.M.: Enhanced release of immunoreactive CGRP and substance P from spinal dorsal horn slices occurs during carrageenan inflammation. Brain Res. 582: 139–142, 1992.

Iadarola, M.J. and Draisci, G.: Elevation of spinal cord dynorphin mRNA compared to dorsal root ganglion peptide mRNAs during peripheral inflammation. In The Arthritic Rat as a Model of Clinical Pain'? ed. by J.M. Beeson and G. Guilbaud, pp. 173–183, Elsevier, Armstedam, 1988.
Katopodis, A.G. and May, S.W.: Novel substrates and inhibitors of peptidylglycine α–amidating monooxygenase. Biochemistry 29: 4541–4548, 1990.
Katopodis, A.G., Ping, D. and May, S.W.: A Novel enzyme from bovine neurointermediate pituitary catalyzes dealkylation of α–hydroxyglycine derivatives, thereby functioning sequentially with peptidylglycine α–amidating monooxygenase in peptide amidation. Biochemistry 29: 6115–6120, 1990.
Katopodis, A.G., Ping, D., Smith C.E. and May, S.W.: Functional and structural characterization of peptidylamidogylocate lyase, the enzyme catalyzing the second step in peptide amidation. Biochemistry 30: 6189–6194, 1991.
Lam, F.Y. and Ferrell, W.R.: Neurogenic component of different models of acute inflammation in the rat knee joint. Ann. Rheum. Dis. 50: 747–751, 1991.
Levine, J.D., Clark, R., Devor, M., Helmes, C., Moskowitz, M.A. and Basbaum, A. I.: Intraneuronal substance P contributes to the severity of experimental arthritis. Science 226: 547–549, 1984.
Li, C., Oldham, C.D. and May, S.W., NN–Dimethyl–1, 4–phenylenediamine as an alternative reductant for peptidylglycine α–amidating mono–oxygenase catalysis. Biochem. J. 300: 31–36, 1994.
Oldham, C.D., Li, C., Girard, P.R., Nerem, R.M. and May, S.W.: Peptide amidating enzymes are present in cultured endothelian cells. Biochem. Biophys. Res. Commun. 184: 323–329, 1992.

(List continued on next page.)

Primary Examiner—Bennett Celsa
(74) Attorney, Agent, or Firm—Needle & Rosenberg, P.C.

(57) ABSTRACT

The invention relates to a method for reducing inflammation in a subject by administering to the subject an effective amount of the compound having the structure I or II:

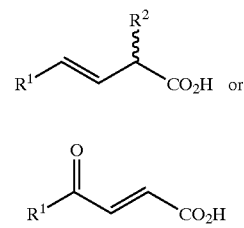

wherein, $R^1$ is $C_1-C_{10}$ branched or straight chain alkyl, aryl, an amino acid, or a peptide; and $R^2$ is hydrogen or lower $C_1-C_5$ branched or straight alkyl, or the salt or ester thereof, wherein the stereochemistry about the carbon-carbon double bond is trans. The invention further relates to a method of inducing an analgesic effect by administering to a subject an effective amount of the compound having the structure I or II. The invention further relates to a compound having the structure II, wherein, $R^1$ is an N-acyl amino acid or peptide, or the salt or ester thereof.

15 Claims, 7 Drawing Sheets

OTHER PUBLICATIONS

Ping, D., Mounier, C.E. and May, S.W.: Reaction versus subsite stereospecificity of peptidyglycine α–monooxygenase and peptidylamidoglycolate lyase, the two enzymes involved in peptide amidation. J. Biol. Chem. 270: 29250–29255, 1995.

Smith, G., Harrison, S., Bowers, J., Weisman, J. and Birch, P.: Non–specific effects of the tachykinin $NK_1$ receptor anatagonist, CP–99,994, in antinociceptive tests in rat, mouse and gerbil. Eur. J. Pharmacol. 271: 481–487: 1994.

Tissot, M., Pradelles, P. and Giroud, J.P.: Substance–P–like levels in inflammatory exudates. Inflammation 12: 25–35, 1988.

Vinegar, R., Truax, J.F., Selph, J.L., Johnston, P.R., Venable, A.L. and McKenzie, K.K.: Pathway to carrageenan–induced inflammation in the hind limb of the rat. Fed. Proc. 46: 118–126, 1987.

Ogonowski, A.A., May, S.W., Moore, A.B., Barrett, L.T., O Bryant, C. L., Pollock, S.H.: Antiinflammatory and analgesic activity of an infibitor of neuropeptide amidation. Journal of Pharmacological and Experimental Therapeutics 280: 846–853, 1997.

Bradbury, A.F., Mistry, J., Roos, B.A. and Smyth, D.G.: 4–Phenyl–3–butenoic acid an in vivo inhibitor of peptidylglycine hyrdroxylase (peptide amidating enzyme). Eur. J. Biochem. 189: 363–368, 1990.

Eipper, B.A., Stoffers, D.A. and Mains, R.E.: The biosynthesis of neuropeptides: Peptide α–amidation. Annu. Rev. Neurosci. 15: 57–85, 1992.

Meuller, G.P., Husten, E.J., Mains, R.E. and Eipper, B.A.: Peptide α–hydroxylation monooxygenase: control by disulfiram. Mol. Pharmacol. 44: 972–980, 1993.

* cited by examiner

METHOD FOR REDUCING INFLAMMATION AND INDUCING AN ANALGESIC EFFECT AND COMPOUNDS THEREOF

BACKGROUND OF THE INVENTION

1. Field of the Invention

The invention relates to a method for reducing inflammation and a method for inducing an analgesic effect in a subject and compounds thereof

2. Background Art

Inflammatory disease represents a pressing public health problem in our society. While rheumatoid arthritis is probably the most widely known chronic inflammatory disease, other examples are ulcerative colitis, Crohn's disease, gout, bursitis and tendinitis. Traditionally, inflammation has been treated with aspirin-like drugs, steroid based compounds, or non-steroidal anti-inflammatory drugs. These drugs are of variable effectiveness; however, they are not therapeutic in nature.

Neuropeptides are released from peripheral terminals of primary afferent sensory nerves and contribute significantly to the inflammatory response of a variety of diseases including rheumatoid arthritis. Examples of neuropeptides that have been investigated extensively are substance P (SP) and Calcitonin Gene-Related Peptide (CGRP). These neuropeptides have been shown to be capable of producing vasodilation, increasing vascular permeability, attracting and activating phagocytic white blood cells, releasing cytokines, lysosomal enzymes and prostaglandins from these cells, increasing the expression of adhesion molecules as well as causing the activation of synoviocytes.

Several pharmacological approaches to reduce the neurogenic component of inflammation have been evaluated; however, a means for reducing inflammation by reducing the release of a. neuropeptide responsible for inflammation has not been developed.

Thus, there remains a need in the art for reducing inflammation in a subject. Applicants have discovered such a method, and have also discovered a method for inducing an analgesic effect in a subject. The prior art does not disclose the methods or compounds such as those described and claimed herein.

SUMMARY OF THE INVENTION

In accordance with the purpose(s) of this invention, as embodied and broadly described herein, this invention, in one aspect, relates to a method for reducing inflammation in a subject, comprising administering to the subject an effective amount of the compound having the structure I or II:

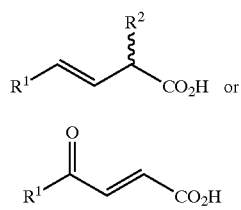

wherein, $R^1$ is $C_1$–$C_{10}$ branched or straight chain alkyl, aryl, an amino acid, or a peptide; and $R^2$ is hydrogen or lower $C_1$–$C_5$ branched or straight alkyl, or the salt or ester thereof, wherein the stereochemistry about the carbon-carbon double bond is trans.

The invention further relates to a method for inducing an analgesic effect in a subject, comprising administering to the subject an effective amount of the compound having the structure I or II:

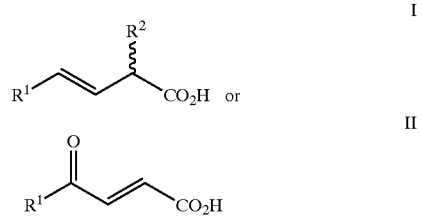

wherein, $R^1$ is $C_1$–$C_{10}$ branched or straight chain alkyl, aryl, an amino acid, or a peptide, and $R^2$ is hydrogen or lower $C_1$–$C_5$ branched or straight alkyl, or the salt or ester thereof, wherein the stereochemistry about the carbon-carbon double bond is trans.

The invention further provides a compound for reducing inflammation and/or inducing an analgesic effect having the structure II:

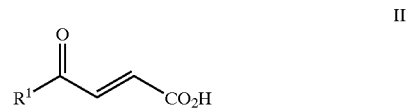

wherein, $R^1$ is an N-acyl amino acid or peptide, or the salt or ester thereof.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

Figure 1:
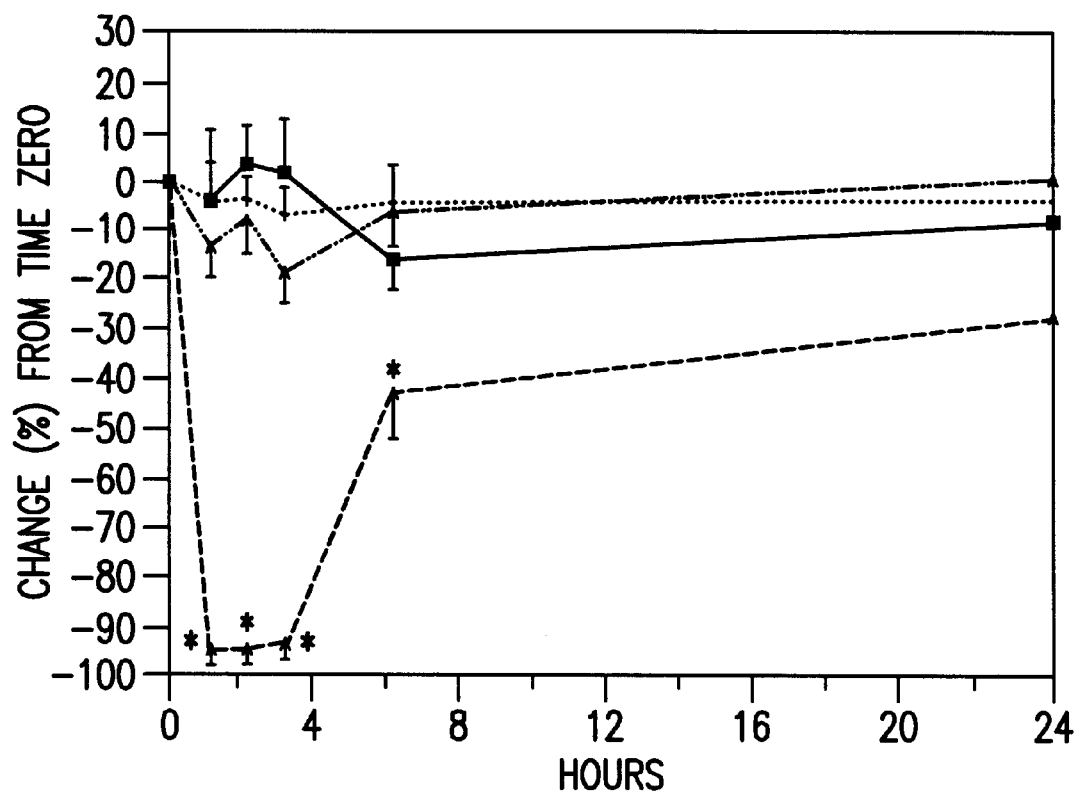
FIG. 1 is a graph showing the effect of trans-4-phenyl-3-butenoic acid (PBA) in vivo on the activity of serum peptidylglycine α-monooxygenase (PAM) and peptidylamidoglycolate lyase (PGL).

Before the present compositions of matter and methods are disclosed and described, it is to be understood that this invention is not limited to specific synthetic methods or to particular formulations, as such may, of course, vary. It is also to be understood that the terminology used herein is for the purpose of describing particular embodiments only and is not intended to be limiting.

In this specification and in the claims which follow, reference will be made to a number of terms which shall be defined to have the following meanings:

The singular forms "a," "an" and "the" include plural referents unless the context clearly dictates otherwise.

In accordance with the purpose(s) of this invention, as embodied and broadly described herein, this invention, in one aspect, relates to a method for reducing inflammation in a subject, comprising administering to the subject an effective amount of the compound having the structure I or II:

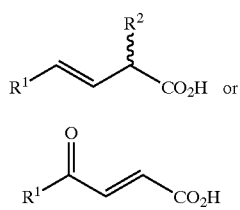

wherein,
$R^1$ is $C_1$–$C_{10}$ branched or straight chain alkyl, aryl, an amnino acid, or a peptide; and
$R^2$ is hydrogen or lower $C_1$–$C_5$ branched or straight alkyl, or the salt or ester thereof, wherein
the stereochemistry about the carbon-carbon double bond is trans.

Neuropeptides contribute significantly to an inflammatory response. Approximately 50% of the known neuropeptides are synthesized as biologically inactive glycine-extended precursors that require a carboxy-terminal post-translational amidation for biological activity. Amidation enzymes are responsible for the conversion of the carboxyl group of the neuropeptide to the corresponding amide group. The term "amidation enzyme" is defined as the enzymes which can convert the carboxyl group of a neuropeptide to an amide group. The two amidating enzymes peptidylglycine α-monooxygenase (EC 1.14.17.3), herein referred to as PAM, and peptidylamidoglycolate lyase (EC 4.3.2.5), herein referred to as PGL, work sequentially to produce an inflammatory neuropeptide from an inactive precursor peptide. The term "inflammatory neuropeptide" is defined as an neuropeptide that plays a biological role in the inflammatory process. Inflammatory neuropeptides can possess a terminal amide group. Examples of these inflammatory neuropeptides include, but are not limited to, substance P (SP) and Calcitonin Gene-Related Peptide (CGRP).

The present invention discloses a method for reducing inflammation in a subject. The term "reducing" refers to a decrease in inflammation or the prevention of further inflammation by an inflammatory neuropeptide. One approach to reduce the inflammation process is to prevent the formation of an active amidated inflammatory neuropeptide from an inactive precursor by inhibiting the amidating enzymes that convert the inactive precursor to the active inflammatory neuropeptide. In one embodiment, inflammation is reduced by inhibiting the amidation of an inactive precursor, preferably a neuropeptide. For example, the inactive neuropeptide undegoes carboxyl-terminal amidation, which converts the inactive neuropeptide to a terminal amidated neropeptide that exhibits biological activity. The process of converting a terminal carboxyl group to a terminal amide is defined as amidation. Amidation also refers to α-amidation, which is a term commonly used in the art.

By inhibiting the activity of an amidating enzyme, the amount of inflammatory neuropeptide that is produced is subsequently reduced. Compounds I and II can inhibit the activity of an amidating enzyme. In one embodiment, the amidating enzyme that is inhibited is peptidylglycine α-monooxygenase (PAM).

It has been discovered that compounds having the structure I and II can inhibit the activity of an amidating enzyme. In the case of a compound having the structure I, when $R^2$ is lower $C_1$–$C_5$ branched or straight alkyl, the alkyl group is stereotopically oriented (R or S configuration) so that it does not interfere with the compound binding to the amidating enzyme. In one embodiment, when the compound has the structure I, $R^1$ is phenyl and $R^2$ is hydrogen. This compound is named trans-4-phenyl-3-butenoic acid, herein referred to as PBA.

In another embodiment, when the compound has the structure II, $R^1$ is an amino acid or peptide. Peptide can also refer to a polypeptide. In another embodiment, when the structure is II, $R^1$ is an N-acyl-amino acid. In yet another embodiment, when the compound has the structure II, the compound is N-acetyl-phenylalanyl-acrylic acid. In yet another embodiment, when the compound has the structure II, $R^1$ is phenyl.

A compound having the structure I and II can inhibit the activity of an amidating enzyme from 10 to 100%. In one embodiment, the lower limit for inhibiting the activity of the amidating enzyme is 10, 20, 30, 40 or 50% and the upper limit is 50, 60, 70, 80, 90 or 100%. The method of the present invention is designed to inhibit the activity of at least one amidating enzyme, more particularly, the enzyme which carries out the first step in the amidation reaction. The inhibition of the amidating enzyme may also occur reversibly or irreversibly. Once again, the selection of the compound having, the structure I or II will determine if the inhibition of the amidating enzyme is reversible or irreversible.

As described above, the method of the present invention reduces inflammation by reducing the amount of an inflammatory neuropeptide. In one embodiment, the method of the present invention reduces the amount of a neuropeptide in a tissue. The tissue can be any tissue that is susceptible to an inflammatory process. In a preferred embodiment, the amount of inflammatory neuropeptide is reduced in a joint, internal organs or other sites susceptible to inflammation.

Upon administration of a compound having the structure I or II, inflammation is immediately reduced in an inflamed tissue. A compound having the structure I and II can reduce inflammation over a short or long period of time depending on the selection of the compound having the structure I or II, the amount administered and the frequence and interval of administration. In one embodiment, inflammation is reduced in the tissue for 0.5 to 12 hours. In another embodiment, the lower limit for inhibition of inflammation is 0.5, 1, 2, 3, 4, 5 or 6 hours and the upper limit of inhibition is 6, 7, 8, 9, 10, 11 or 12 hours. As described above, inflammation is inhibited by reducing the amount of an inflammatory neuropeptide present in a tissue. In one embodiment, the amount of inflammatory neuropeptide in an inflamed tissue of a subject is reduced from 10 to 100%. In another embodiment, the lower limit for reduction of an inflammatory neuropeptide in a tissue is 10, 20, 30, 40, 50% and the upper limit is 50, 60, 70, 80, 90, 95 or 100%. Moreover, a compound having the structure I and II can be administered concurrently or sequentially to reduce inflammation in a subject.

The invention further relates to a method for inducing an analgesic effect in a subject, comprising administering to the subject an effective amount of a compound having the structure I or II:

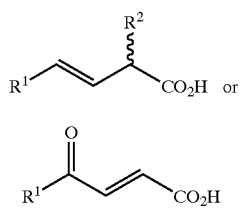

wherein,
$R^1$ is $C_1$–$C_{10}$ branched or straight chain alkyl, aryl, an amino acid, or a peptide; and
$R^2$ is hydrogen or lower $C_1$–$C_5$ branched or straight alkyl, or the salt or ester thereof, wherein
the stereochemistry about the carbon-carbon double bond is trans.

In one embodiment, a compound having the structure I and II can induce an analgesic effect in a subject. In yet another embodiment, a compound having the structure I and II can induce an analgesic effect and reduce inflammation in a subject. Moreover, a compound having the structure I and II can be administered concurrently or sequentially to reduce inflammation and induce an analgesic effect in a subject.

The site of action of the analgesic effect can be central or peripheral. Mediators involved in the production of peripheral pain include, but are not limited to, neuropeptides, bradykinin, and prostaglandins. Examples of neuropeptides, in particular, inflammatory neuropeptides that produce peripheral pain, include, but are not limited to, Substance P and Calcitonin Gene-Related Peptide. Examples of prostaglandins are known in the art.

The methods and compounds of the present invention can reduce inflammation and/or induce an analgesic response in a subject. In one embodiment, the subject is a mammal, reptile, bird or fish. In another embodiment, the subject can be a human or another animal, wherein the animal can particularly be a domestic, food producing or wild animal. Examples of domestic animals include but are not limited to dogs, cats, horses or birds. Examples of food producing animals include but are not limited to cows, pigs, chickens or sheep. Examples of wild animals include but are not limited to lions, tigers, elephants, monkeys or bears.

As used herein to describe the present anti-inflammatory and analgesic methods, "an effective amount" of a compound is that amount capable of achieving the desired effect. As described above, an effective amount can be an amount sufficient to reduce inflammation and/or induce an analgesic effect. Such amounts can readily be determined for any specific composition using standard methods and as described herein.

The exact amount of the compound having the structure I or II required to reduce inflammation and/or induce an analgesic effect will vary from subject to subject, depending on the species, age, weight and general condition of the subject, the severity of the disease, infection or condition that is being treated or prevented, the particular compound used, its mode of administration, and the like. Thus, it is not possible to specify an exact amount. However, an appropriate amount may be determined by one of ordinary skill in the art using only routine experimentation given the teachings herein. In one embodiment, the amount of a compound having the structure I or II that is administered is from 10 to 1000 mg/kg bodyweight of the subject. In another embodiment, the lower limit is 10, 20, 30, 40, 50, 60, 70, 80, 90, 100, 200 or 300 mg/kg bodyweight of the subject and the upper limit is 300, 400, 500, 600, 700, 800, 900 or 1000 mg/kg bodyweight of the subject. A single administration may be sufficient, depending upon the condition being treated or prevented; however, it is also contemplated that multiple administrations may be administered. Administrations after the initial administration may be of lower dosage than the initial dosage.

The anti-inflammatory and/or analgesic compounds having the structure I and II can be administered to a subject using a variety of methods known in the art. In one embodiment, the compounds can be delivered parenterally, by injection, such as intramuscular, intraperitoneal, intravenous or subcutaneous injection, or by inhalation. In another embodiment, when the mode of administration of a compound having the structure I or II is by oral delivery, and $R^1$ is an amino acid or peptide, then $R^1$ should preferably be a D-amino acid(s) or a peptidomimetic. A peptidomimetic useful in the present invention is a compound derived from a peptide or protein. Peptidomimetics bridge the gap between simple peptides and the nonpeptide synthetic structures and, as such, may be useful in delineating pharmacophores and facilitate the translation of a peptide into small nonpeptide compounds. A peptidomimetic can also be an organic molecule that mimicks a property of a peptide ligand.

Depending on the intended mode of administration, a compound having the structure I or II can be in pharmaceutical compositions in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of a compound having the structure I or II, possibly in combination with a pharmaceutically acceptable carrier and, in addition, may include other medicinal agents, pharmaceutical agents, carriers, adjuvants, diluents, etc.

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration, if used, is generally characterized by injection. Injectables can be prepared in conventional forms, either as liquid solutions or suspensions, solid forms suitable for solution or suspension in liquid prior to injection, or as emulsions.

The invention further relates to a compound for reducing inflammation and/or inducing an analgesic effect having the structure II:

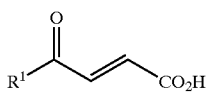

wherein, $R^1$ is an N-acyl amino acid or peptide,
or the salt or ester thereof

In one embodiment, the compound having the structure II is N-acetyl-phenylalanyl-acrylic acid.

A general procedure for preparing compounds having the structure II can be found in Scheme A.

Scheme A

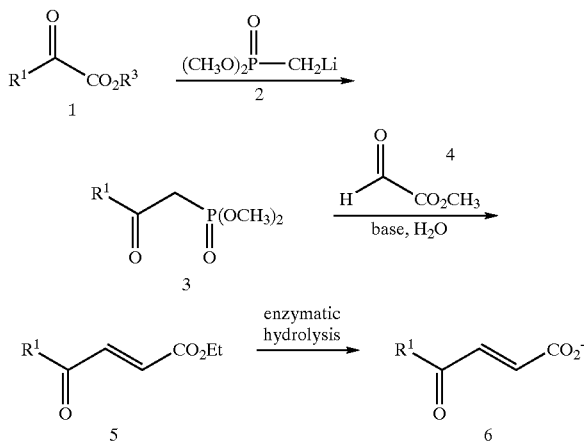

Treatment of the ester 1, wherein $R^1$ is $C_1$–$C_{10}$ branched straight chain alkyl, aryl, a residue of an amino acid or peptide and $R^3$ is $C_1$–$C_5$ branched or straight chain alkyl or aryl, with the phosphodiester compound 2 results in the formation of compound 3. The addition of 4 to 3 in the presence of a base followed by hydrolysis produces the α,β-unsaturated ester 5. Enzymatic hydrolysis of 5 produces the acid compound 6, which can readily be converted to the salt using techniques known in the art.

The present invention may be understood more readily by reference to the following detailed description of preferred embodiments of the invention and the Examples included therein.

EXAMPLES

Synthesis of N-Ac-LPhe-Acrylic Acid

The synthesis of N-Ac-L-Phe-acrylic acid is shown below in Scheme B. To a solution of N-Ac-L-Phe (5.0 g, 24.1 mmol) in 120 ml of ethanol was added a few drops of concentrated HCl. The reaction mixture was refluxed overnight, then concentrated under reduced pressure. The residual solid was dissolved in ethyl acetate, washed twice with dilute NaHCO$_3$, then once with water. The organic phase was dried over MgSO$_4$, concentrated under reduced pressure, and dried under vacuum, to give N-Ac-Phe-OEt (7) as a white solid.

n-Butyllithium (117.0 ml, 42.5 mmol) was slowly added to a solution of dimethyl methylphosphonate (4.6 ml, 42.4 mmol) in 50 ml anhydrous THyF kept at −78° C., under a nitrogen atmosphere. The reaction mixture was stirred, at −78° C. for 15 minutes, at which time a precipitate formed to produce compound 8. N-Ac-Phe-OEt (5.0 g, 21.2 mmol) is then added all at once. The reaction mixture was slowly brought to room temperature, and stirred overnight (the reaction was monitored by TLC (eluting solvent EtOAc)). The reaction was then quenched by the addition of water. Ether was then added, the two layers separated, and the aqueous layer extracted with ether. The ether extracts were discarded. The aqueous layer was then acidified by the addition of 4 N HCl and extracted with methylene chloride. The combined methylene chloride extracts were dried over MgSO$_4$, filtered, and concentrated under reduced pressure. The product, N-Ac-L-Phe-α-ketophosphonate (9), was purified by flash chromatography (eluting solvent: CHCl$_3$/MeOH 10:1), to give pure bright yellow oil (5.0 g, 16.1 mmol, 76%).

A mixture of methyldimethoxyacetate (10.0 g, 74.5 mmol), glyoxilic acid monohydrate (6.8 g, 73.9 mmol), and a catalytic amount of p-toulenesulfonic acid was stirred at 80° C. overnight. The reaction mixture is then cooled to 0° C., and P$_2$O$_5$ (7.8 g) was slowly added. The thick slurry was then stirred at 80° C. for 4 hours and distilled under vacuum to afford methylglyoxylate, as a yellow oil which quickly thickens and turns clear.

Potassium carbonate (4.45 g, 32.2 mmol) dissolved in 20 ml water was added to a mixture of N-Ac-Phe-α-ketophosphonate (5.04 g, 16.1 mmol) and methylglyoxylate (1.4 g, 15.9 mmol) in 10 ml water at 5° C., at which time a precipitate formed immediately. The reaction mixture was stirred at 5° C. for 15 minutes. The solid methyl N-Ac-L-Phe acrylate (11) was then collected by suction, washed with cold water, dried under vacuum over P$_2$O$_5$, and recrystallized from hot ethyl acetate/hexane, yielding 1.3 g (4.72 mmol, 29%) of pale yellow solid.

To a solution of methyl N-Ac-L-Phe acrylate (0.5 g, 1.81 mmol) in 7 ml of methanol is added 75 ml of 0.1 M phosphate buffer, pH 7.0, at which time the solution turns cloudy. Pig Liver Esterase (5000 U) was then added and the reaction mixture stirred vigorously at 30° C. for 48 hours (the reaction mixture is then clear; the progress of the reaction is monitored by TLC, eluting solvent: EtOAc). The reaction mixture was then washed twice with ether (an emulsion forms, ether extracts discarded), acidified by the addition of 4 N HCl (turns cloudy), and saturated with NaCl. The aqueous layer was then thoroughly extracted with methylene chloride (an emulsion forms). The combined organic extracts were dried over MgSO$_4$, concentrated under reduced pressure, and dried under vacuum to give N-Ac-L-Phe-acrylic acid (12) as a white solid (0.255 g, 0.98 mmol, 54%). Elemental Analysis: Calculated for $C_{14}H_{15}NO_4+1/4H_2O$; C, 63.27%; H, 5.88%; N, 5.27%; Found: C, 63.26%; H, 5.85%; N, 5.22%. $^1$H NMR (DSMO-d$_6$ DMSO−2.49 ppm): δ 8 1.78 (s, 3H); 2.72–3.07 (m, 2H); 4.70, (m, 1H); 6.56 (d, 1H, J=15.9 Hz); 7.09 (d, 1H, J=15.9 Hz); 7.22 (m, 5H); 8.42 (d, 1H). M.P.: decomposes. MS (FAB+): 262.3 (M+1).

Scheme B

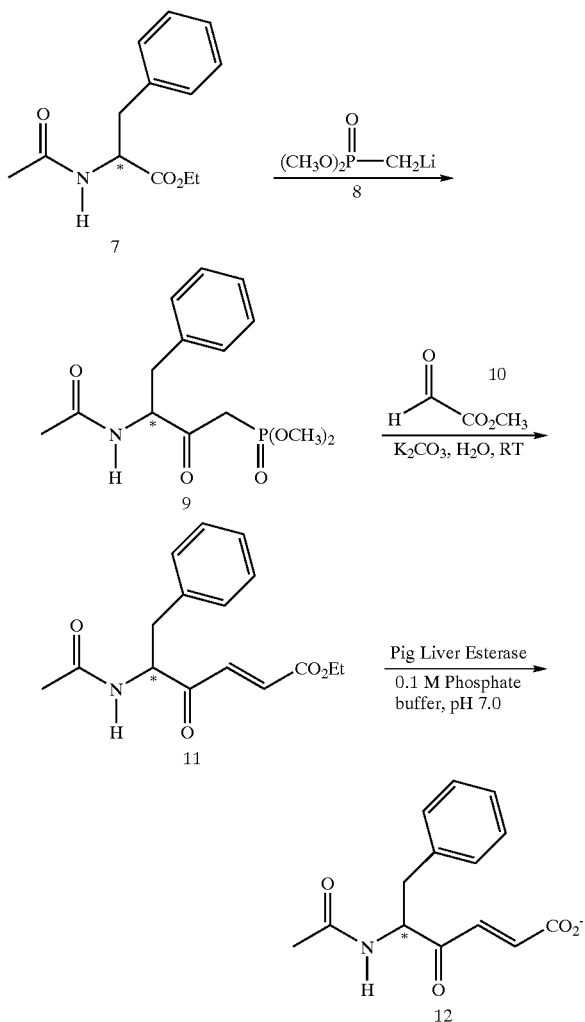

Experimental Animals

Adult male, Sprague Dawley rats (175–225 g) and male ND4 Swiss Webster mice (18–20 g) were purchased from Harlan Sprague Dawley, Inc. (Indianapolis, Ind.), housed in appropriate caging facilities and allowed food and water ad libitum. All experiments using animals were approved by the Institutional Animal Care and Use Committee of Mercer University (Macon, Ga.).

Drugs and Reagents

PBA used in all experiments was purchased from Aldrich Chemical Co. (Milwaukee, Wis.) and recrystallized from hot ethyl acetate. For all injections, PBA was dissolved in saline, the pH adjusted with sodium hydroxide to 7.5 and administered subcutaneously (between the scapulae) using a constant volume (2 ml/kg). Type IV, lambda carrageenan, bradykinin acetate, serotonin hydrochloride, phenyl-p-quinone and acetylcholine chloride were all purchased from Sigma Chemical Co (St. Louis, Mo.). Bovine liver catalase (65,000 units/mg) was purchased from Boehringer Mannheim (Indianapolis, Ind.). α-Hydroxyhippuric acid was purchased from Aldrich and recrystallized before use. TNP-D-Tyr-Val-Gly was synthesized as disclosed in Katopodis and May (*Biochemistry* 29, 4541–4548, 1990). All other reagents, solvents and chemicals were of analytical grade.

Evaluation of PAM and PGL Activity

Male rats were fasted overnight and anesthetized with ether to obtain blood samples for measuring PAM and PGL activity in serum. Blood (0.5 ml) was collected from the tail vein at different times and spun at 14,000×g for 5 minutes. Serum was collected and stored at −70° C. until assayed. PAM activity was determined based on the procedure disclosed in Katopodis et al. (*Biochemistry* 30, 6189–6194, 1991). Briefly, 50 μl of serum sample (enzyme source) was added to 200 μl of the assay mixture which contained tripeptide TNP-D-Tyr-Val-Gly as the enzyme substrate (40 μM), copper sulfate (15 μM), L-ascorbate (4 mM) and catalase (1 mg/ml) in MES buffer (100 mM, pH 6.5). After a 30 minute incubation period at 37° C., an aliquot (90 μl) was quenched with 10 μl of $HClO_4$ (3M) and centrifuged at 14,000×g for 5 minutes. A 20 μl aliquot was removed and used to assay for product using reverse phase HPLC at 344 nm on a C8 column with a mobile phase of 56% water/0.1% trifluoroacetic acid/44% acetonitrile at a flow rate of 1.5 mL/min. In this manner, both TNP-D-Tyr-Val-$NH_2$ as well as the TNP-D-Tyr-Val-α-hydroxyGly were quantitated simultaneously. PGL activity was assayed by measuring the conversion of α-hydroxyhippuric acid to benzamide as disclosed in Katopodis and May (*Biochemistry* 29, 4541–4548, 1990). Briefly, 50 μl of the serum sample was added to 200 μl of a 100 mM MES buffer solution (pH 6.5) containing 2 mM of the enzyme substrate. After incubation for 30 minutes at 37° C., an aliquot of the assay mixture was quenched with 3 M $HClO_4$, centrifuged at 14,000×g and 20 μl used to analyze for benzamide product by HPLC using a C8 reverse phase column. Product detection was performed at 225 nm using a mobile phase of 80% water/0.1% trifluoroacetic acid/20% acetonitrile at a flow rate of 1.5 mL/min. Enzyme activity was expressed as milliunits per milliliter which is the amount of enzyme required to produce one nanomole of product.

Carrageenan Edema, Bradykinin and Serotonin Edemas

Carrageenan, bradykinin and serotonin edemas were induced in anesthetized, male Sprague-Dawley rats (150–175 g) by injecting 0.5 mg (0.05 ml) of carrageenan, 50 μg (0.1 ml) of bradykinin and 20 μg (0.1 ml) of serotonin, respectively, into the subplantar region of the left hind paws the contralateral hind paws received saline only. Hind paw volumes (edema) were measured plethysmographically by displacement of mercury at 0, 1, 2, 3, 4 and 6 hours post administration of carrageenan, 30 minutes after bradykinin and 1 hour after serotonin. Swelling was determined by subtracting the volume (ml) of the right hind . paw from that of the left. PBA was administered subcutaneously 30 minutes before the administration of carrageenan and serotonin and one hour before bradykinin. In those experiments in which PBA was delivered continuously to rats over a 7 day period prior to the administration of carrageenan, ALZET osmotic pumps (Palo Alto, Calif.) were filled with drug and implanted subcutaneously between the scapulae into anesthetized rats.

Extraction and Quantitation of SP Levels

The effects of PBA on levels of SP were evaluated using a modification of a method previously disclosed in Ahmed et al. (*Peptides* 15, 317–322, 1994). Briefly, at different times following the administration of carrageenan, hind paw ankle joints were removed, immediately frozen on dry ice and stored at −80° C. until assayed for SP. After the frozen sample was weighed, it was boiled for 7 minutes as a 10% w/v solution of 2M acetic acid in 4% EDTA, pH 3.5, cut into small pieces and boiled for an additional 7 minutes. Samples were then homogenized for 60 seconds in a Brinkmann Polytron (Westbury, N.Y.), sonicated for 30 seconds and centrifuged at 3000×g for 20 minutes. Supernatants were lyophilized and then diluted in radioimmunoassay (RIA) buffer prior to analysis. SP levels were determined from these samples by using a commercially available RIA kit (INCSTAR, Stillwater, Minn.). Initial experiments conducted to insure the specificity of the substance P antibody for SP found the cross-reactivity for the glycine-extended precursor to be 1.7% at concentrations up to 100 nanograms/ml.

Analgesic Assays

The effects of PBA on the perception of pain was evaluated using several different animal models. The spinally-mediated tail-flick response to heat in fasted rats (250–290 g) was used by measuring the withdrawal latency following immersion of the rodent's tail (2") into hot water (50° C.). PBA at several different dose levels was administered subcutaneously and the time to tail withdrawal was measured at 0, 15, 30 and 60 minutes post-drug administration. The analgesic effects of PBA were also evaluated in fasted mice following the injection of either phenyl-p-quinone or acetylcholine. Male, ND4 Swiss mice (15–20 g) were dosed subcutaneously with PBA or saline followed immediately by the injection of phenyl-p-quinone (2 mg/kg i.p.). After 5 minutes, the number of writhes (abdominal constrictions along with contortion of the trunk and extension of the hindlimbs) was counted over the next 10 minutes. When acetylcholine (6 mg/kg i.p.) was used as the noxious agent, PBA was administered subcutaneously 15 minutes before the administration of the algesic agent. The number of writhes produced was counted over the last 5 minutes following the algesic agent.

Statistical Analysis

Data are presented as mean responses±S.E.M. Two way analysis of variance for repeated measures was used to test for significance. Comparison of means was performed by using Tukey's post hoc tests. A probability of $P<0.05$ was considered statistically significant.

Reduction of Inflammation by PBA

Figure 2:
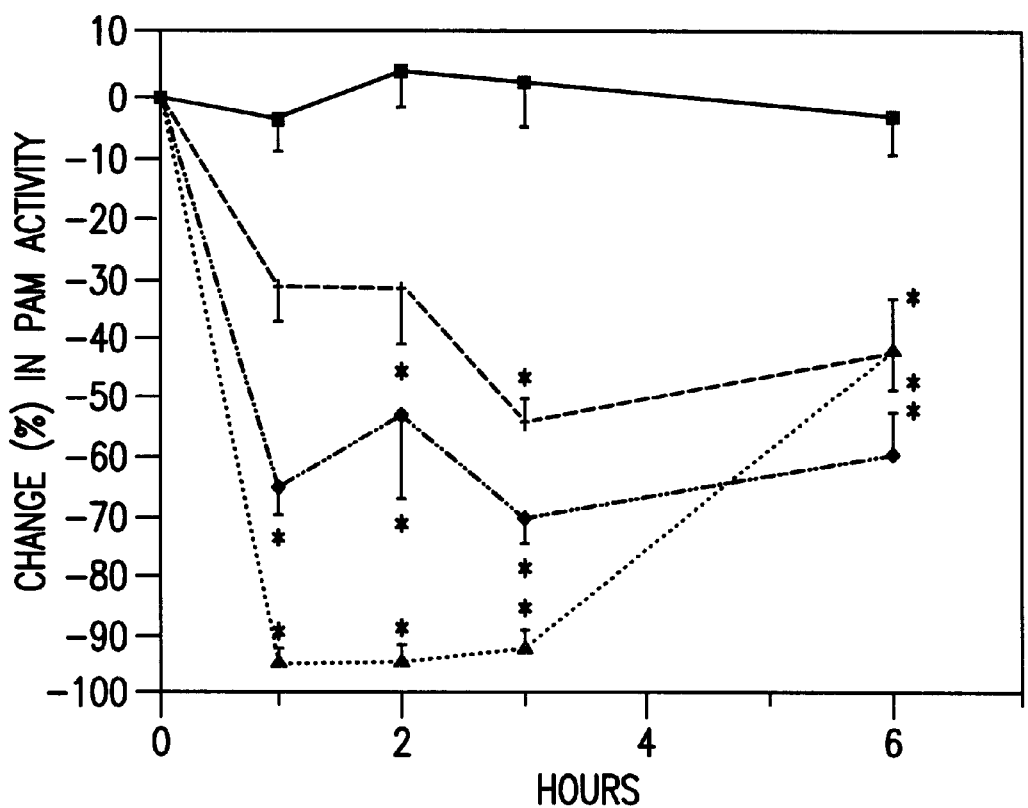
FIG. 2 is a graph showing the dose-response effect of PBA on serum PAM activity in normal rats.

Experiments were conducted to determine if the effects of PBA on PAM and PGL activity in vivo were similar to those observed in vitro. As shown in FIG. 1, PBA (500 mg/kg s.c.) significantly inhibited (>90%) the activity of PAM in serum within 1 hour following the administration of a single dose to conscious rats. This magnitude of inhibition remained during the first 3 hours following administration, decreased to 43% inhibition by 6 hours, and was not significantly different from control values after 24 hours. This same dose of PBA had no effect on serum PGL activity during the 24 hour observation period demonstrating the ability of PBA to selectively inhibit PAM activity. This inhibitory effect of PBA on serum PAM activity was also found to be dose-related (FIG. 2) with the 50 and 150 mg/kg doses having similar time-courses of inhibition but of lesser magnitude than the effects caused by the 500 mg/kg dose.

Figure 3:
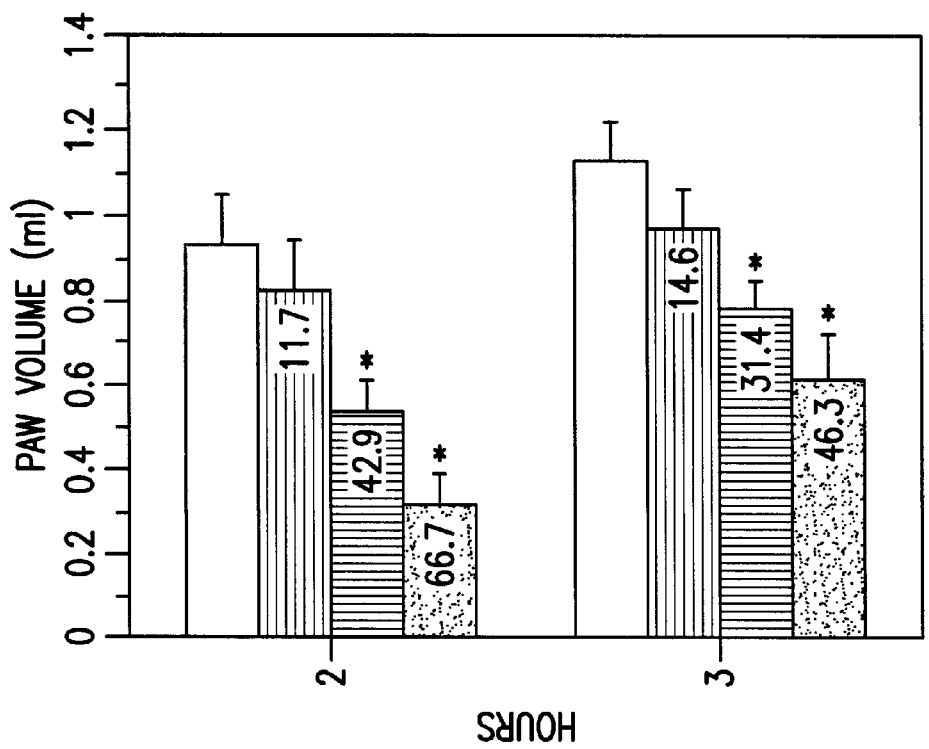
FIG. 3 is a graph showing the effect of PBA on carrageenan-induced edema in rats.

These results show that PBA is capable of producing an anti-inflammatory effect in vivo since inhibition of PAM activity would result presumably in lowering of endogenous levels of amidated neuropeptides such as SP and CGRP. Therefore, experiments were conducted to determine if PBA had any effect on inflammation induced by the subplantar injection of carrageenan. As seen in FIG. 3, the subcutaneous administration of PBA 30 minutes before the phlogistic agent produced a dose-related inhibition of hind paw edema at 2 and 3 hours post-administration of the phlogistic agent. This inhibitory effect was greatest at 2 hours with the 250 and 500 mg/kg doses producing 43 and 67% inhibition, respectively. A similar time-course of inhibition of carrageenan edema was observed in these animals following i.p administration of PBA.

Bradykinin and serotonin are two mediators released early during acute inflammation, and have been suggested to play an important role during the early phase of carrageenan edema. Because PBA appeared to be more effective during the early phase of carrageenan edema, experiments were conducted to determine if PBA was capable of inhibiting hind paw swelling produced by these two mediators. It is clear from the data shown in Table 1 that PBA lacked significant inhibitory activity on edema produced by either bradykinin or serotonin at a dose that produced significant inhibition of carrageenan edema.

TABLE 1

| | Hind Paw Volume (mL ± S.E.M.) | | |
|---|---|---|---|
| Phlogistic Agent | Controls | PBA | Inhibition (%) |
| Carrageenan[a] | 0.93 ± 0.12 | 0.31 ± 0.07 | 66.7[b] |
| Bradykinin[c] | 0.39 ± 0.05 | 0.29 ± 0.04 | 25.6 |
| Serotonin[d] | 0.81 ± 0.07 | 0.66 ± 0.03 | 18.5 |

Male, Sprague-Dawley rats were dosed with PBA s.c. 30 minutes before carrageenan and serotonin and 1 hour before bradykinin. Hind paw volumes were measured plethysmographically by displacement of mercury.
[a]Carrageenan (0.05 mL of 1% solution) was injected into left hind paw. Right hind paw received saline. Paws were measured 2 hours after phlogistic agent.
[b]Statistical significance ($P < .05$) compared to controls; n = 8 for each assay.
[c]Bradykinin (50 µg) was injected into the left hindpaw. Paws were measured 30 minutes after the phlogistic agent.
[d]Serotonin (20 µg) was injected into the left hindpaw. Paws were measured 1 hour after phlogistic agent.

Figure 4:
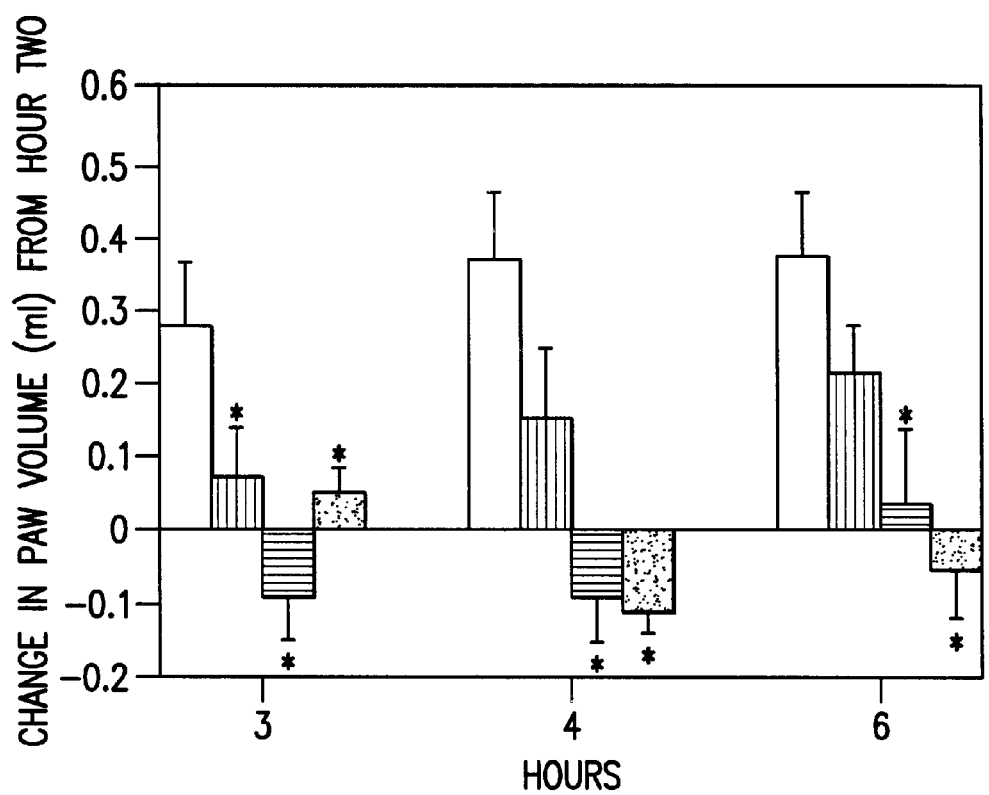
FIG. 4 is a graph showing the effect of PBA on carrageenan edema when administered two hours after the administration of the phlogistic agent.

The reduced effectiveness observed with PBA during the late phase of carrageenan edema (at 3 hours) could be due to the drug having a short duration of action rather than a lack of activity. To evaluate this possibility, PBA Was administered to animals 2 hours after the induction of inflammation. As seen in FIG. 4, PBA inhibited the continuous increase in hind paw swelling observed in control animals at 3, 4 and 6 hours post-administration of the phlogistic agent. The 100 mg/kg dose was only effective at hour 3 while the 250 and 500 mg/kg doses produced significant inhibition of hind paw swelling for up to 6 hours post-phlogistic agent.

Since these results suggested that the pharmacokinetics of PBA were responsible for its short duration of action in carrageenan edema, experiments were conducted in which PBA was administered to rats via osmotic pumps to prolong its duration of action. Initial experiments using this method of drug delivery were designed to determine if continuous release of PBA (50 to 100 mg/kg/hr s.c.) over a 7 day period would produce a sustained reduction in serum PAM activity. Serum samples were taken every other day for analysis of PAM activity. Results from this study demonstrated that this method of dosing with PBA produced a sustained reduction (>75%) in PAM activity throughout the 7 day dosing period.

Figure 5A:
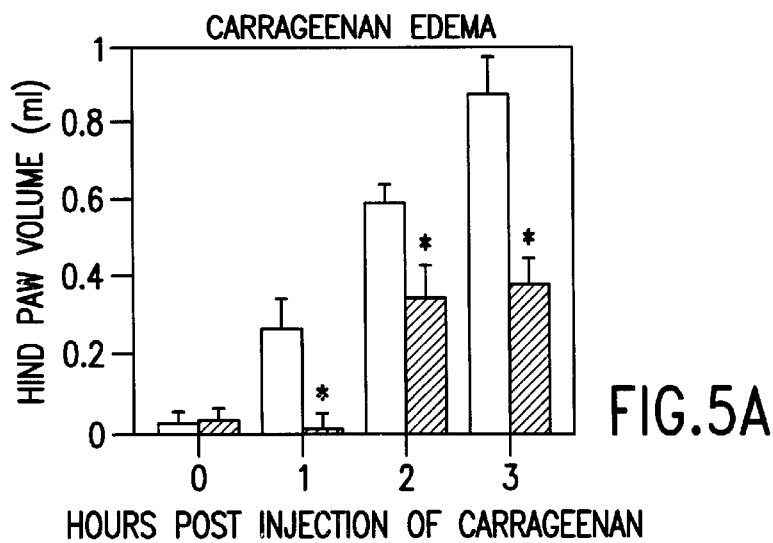
FIG. 5 is a graph showing the effect of continuous administration of PBA on carrageenan edema, serum PAM activity and SP levels in rat hind paws.
Figure 5B:
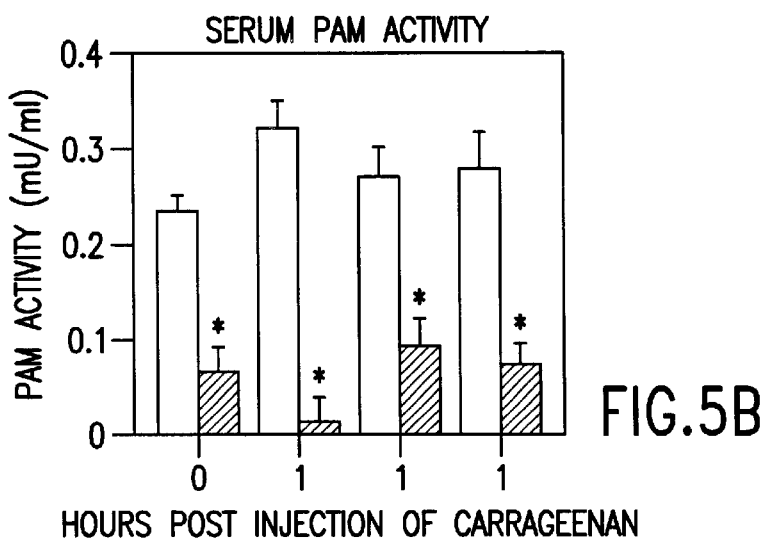
Figure 5C:
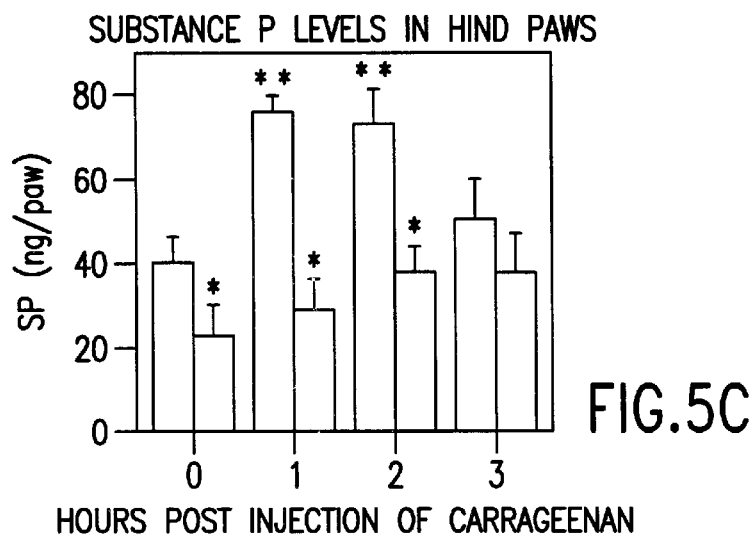

Based on these results, this same dosing protocol was used to evaluate the effects of PBA on carrageenan edema in animals. Animals were treated with PBA (75 mg/kg/hr) for 1 week, and then carrageenan was administered into the subplantar region of the hind paw. The degree of inflammation as well as serum PAM activity and SP levels in hind paw tissue were measured at different time periods. Results of these experiments are shown in FIG. 5. As expected, carrageenan produced a time-dependent increase in hind paw volume in control animals which reached a peak 3 hours post-administration of the phlogistic agent (FIG. 5a). While serum PAM activity did not change significantly in these animals (FIG. 5b), there was a significant increase in levels of SP in the inflamed hind paws during the first 2 hours after carrageenan administration (FIG. 5c). Interestingly, in animals treated for 7 days with PBA, both serum PAM activity and SP levels in hind paw tissue were significantly reduced compared to controls when measured prior to the administration of carrageenan (FIGS. 5b and c, time 0). In those animals treated with PBA, there was a significant inhibition of carrageenan edema at each time period (FIG. 5a). This inhibition of hind paw swelling by PBA correlated with its ability to inhibit serum PAM activity and reduce SP levels in hind paw tissue of animals administered carrageenan (FIGS. 5b and c).

The results of the studies with PBA in carrageenan edema clearly demonstrate that PBA is capable of inhibiting an acute inflammatory response. These results illustrate that the enzyme PAM may be an attractive target for the pharmacological control of acute inflammation.

Induction of an Analgesic Effect by PBA

Since most anti-inflammatory drugs also have analgesic activity, experiments were conducted to determine if PBA possessed the ability to increase the threshold to pain. Initial experiments were performed using the rodent tail-flick assay to determine if PBA possessed any central analgesic activity following acute administration. After obtaining baseline values, PBA was administered subcutaneously to rats followed by immersion of the rodent tail into 50° C. water and measuring the time to tail withdrawal at 15, 30 and 60 minutes post-drug administration. In these experiments, PBA did not have any effect on time to tail withdrawal at any time period with doses up to 750 mg/kg.

Figure 6:
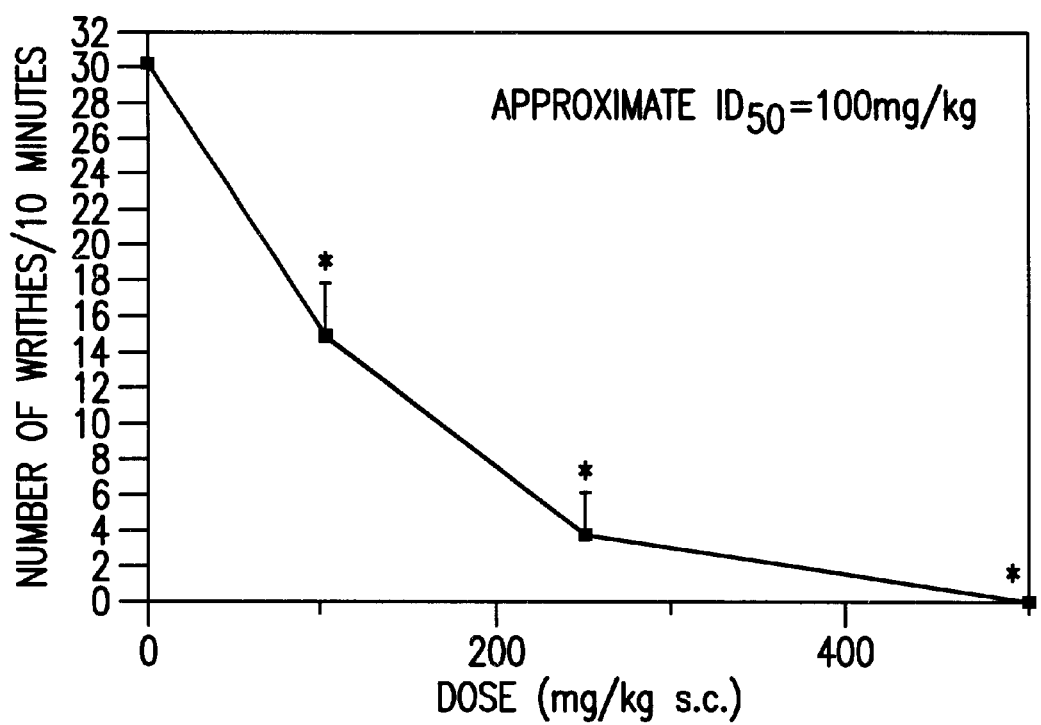
FIG. 6 is a graph showing the effect of PBA on phenyl-p-quinone-induced writhing in mice.
Figure 7:
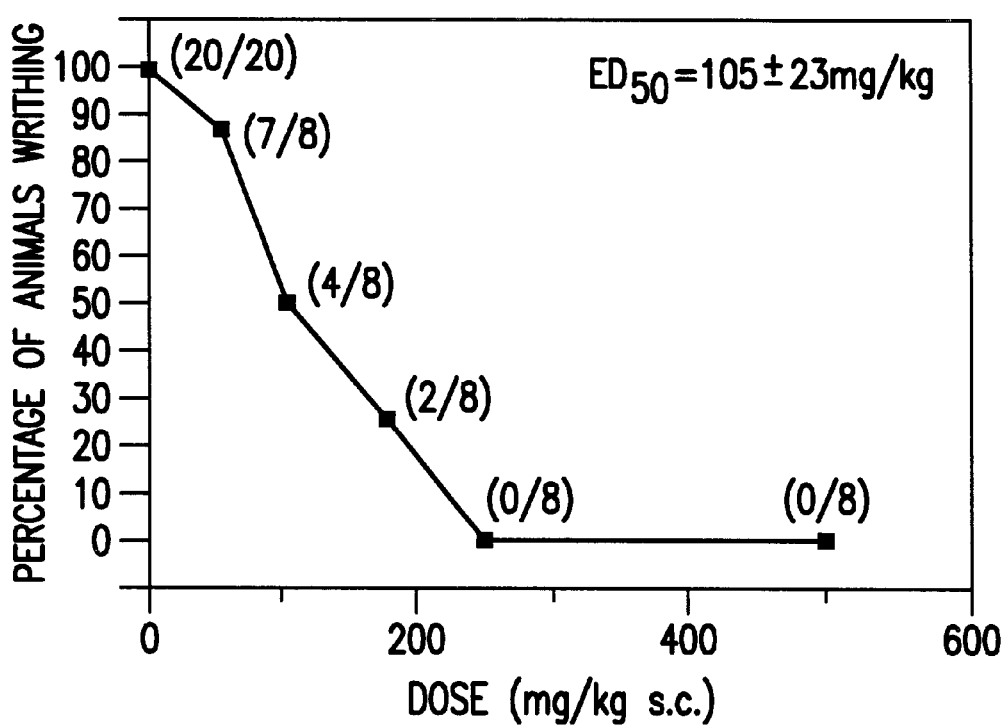
FIG. 7 is a graph showing the effect of PBA on acetylcholine-induced writhing in mice.

The phenyl-p-quinone and acetylcholine-induced writhing assays in mice are known to be inhibited by both central as well as peripheral-acting analgesic agents based on the disclosure of Gyires and Torma (*Arch. Int. Pharmacodyn.* 267, 131–140, 1984). The i.p. injection of these two substances produces painful responses (writhes) as manifested by a series of abdominal constrictions with contortions of the trunk and extension of the hindlimbs. Since PBA lacked central analgesic activity, these two assays were used to evaluate the peripheral analgesic activity of PBA. As seen in FIG. 6, PBA produced a significant dose-related inhibition of phenyl-p-quinone-induced writhing with greater than 85% inhibition of writhing occurring at 250 mg/kg. In the acetylcholine-induced writhing assay, because the number of writhes produced in each control animal was small (1 to 8), the effects of PBA were expressed as the percentage of animals per group that writhed (all or none response) at each dose level (FIG. 7). Again, PBA showed significant inhibitory activity with an $ED_{50}$ of 105 mg/kg which is similar to the dose of PBA that reduced phenyl-p-quinone-induced writhing by 50%. It is noteworthy that the 100 mg/kg dose which did not show any activity on carrageenan edema produced a significant analgesic effect in both writhing assays.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A method for reducing inflammation in a subject, comprising administering to the subject an effective amount of a compound having the structure II:

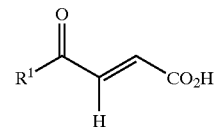

wherein,
$R^1$ is an L-amino acid, or an L-amino acid containing peptide; and
wherein the stereochemistry about the carbon-carbon double bond is trans.

2. The method of claim 1, wherein $R^1$ is an N-acyl-amino acid.

3. The method of claim 1, wherein the compound having the structure II is N-acetyl-phenylalanyl-acrylic acid.

4. The method of claim 1, wherein the inflammation is reduced by inhibiting amidation of a neuropeptide.

5. The method of claim 1, wherein the compound inhibits amidation of a neuropeptide.

6. The method of claim 5, wherein the compound inhibits amidation by inhibiting an amidating enzyme.

7. The method of claim 6, wherein the amidating enzyme is PAM.

8. The method of claim 6, wherein the compound inhibits amidating enzyme activity from 10 to 100%.

9. The method of claim 1, wherein the compound reduces inflammation by reducing the amount of an inflammatory neuropeptide of from 1 to 100%.

10. The method of claim 9, wherein the compound reduces the amount of an inflammatory neuropeptide in a tissue of the subject.

11. The method of claim 10, wherein the tissue is a tissue susceptible to an inflammatory process.

12. The method of claim 10, wherein the tissue is in an inflamed joint.

13. The method of claim 1, wherein the mode of administration comprises oral, intraveneous injection, intraperitoneal injection or intramuscular injection.

14. The method of claim 1, wherein the effective amount of the compound is from 10 to 1000 mg/kg bodyweight of the subject.

15. The method of claim 1, wherein the subject is a human or non-human animal.

* * * * *

UNITED STATES PATENT AND TRADEMARK OFFICE
CERTIFICATE OF CORRECTION

PATENT NO. : 6,495,514 B1
DATED : December 17, 2002
INVENTOR(S) : Sheldon W. May et al.

It is certified that error appears in the above-identified patent and that said Letters Patent is hereby corrected as shown below:

Title page,
Item [73], Assignee, the phrase "Mercer University, Macon, GA (US)" should be deleted and the phrase -- Georgia Tech Research Corporation, Atlanta, GA (US) and Mercer University, Macon, GA (US) -- should be inserted therefore.

Signed and Sealed this

Fourth Day of May, 2004

JON W. DUDAS
*Acting Director of the United States Patent and Trademark Office*